Figure 1:
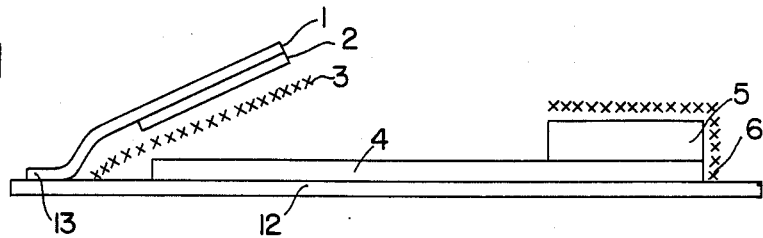

United States Patent [19]

Deneke et al.

[11] Patent Number: 4,665,023

[45] Date of Patent: May 12, 1987

[54] IMIDAZOLE DERIVATIVES AS REDOX INDICATORS

[75] Inventors: Ulfert Deneke, Rimbach-Zotzenbach; Werner Güthlein, Mannheim; Manfred Kuhr, Mannheim; Hartmut Merdes, Heidelberg; Hans-Rüdiger Murawski, Lampertheim; Hans Wielinger, Weinheim, all of Fed. Rep. of Germany

[73] Assignee: Boehringer Mannheim GmbH, Mannheim, Fed. Rep. of Germany

[21] Appl. No.: 717,511

[22] Filed: Mar. 29, 1985

[30] Foreign Application Priority Data

Mar. 31, 1984 [DE] Fed. Rep. of Germany ....... 3411997

[51] Int. Cl.$^4$ ...................... C12Q 1/28; C07D 455/04
[52] U.S. Cl. ...................... 435/28; 436/135; 546/94; 546/165; 548/119; 548/336; 548/342; 548/343; 548/346
[58] Field of Search .............. 548/346, 336, 342, 343, 548/119; 546/94, 165; 435/28; 436/135

[56] References Cited

U.S. PATENT DOCUMENTS 4,472,406 9/1984 Gerster .............................. 546/94 X
4,535,165 8/1985 Moore .............................. 548/346 X
4,567,177 1/1986 Bigg et al. ........................ 546/94 X

OTHER PUBLICATIONS

Chemical Abstracts, 68:29637c (1968), [Krieg, B. et al., Chem. Ber., 100(12), 4042–4049, (1967)].
B. Krieg et al., Chem. Ber., 100: 4042–4049, (1967).

Primary Examiner—Richard A. Schwartz
Attorney, Agent, or Firm—Felfe & Lynch

[57] ABSTRACT

The present invention provides imidazole derivatives of the general formula:

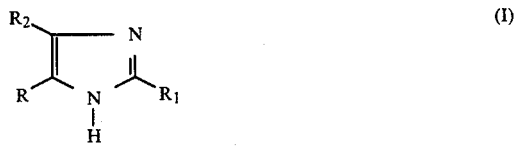

wherein R, $R_1$ and $R_2$ are defined hereinbelow.

The present invention is also concerned with processes for the preparation of these imidazole derivatives and with the use thereof as redox indicators.

13 Claims, 4 Drawing Figures

IMIDAZOLE DERIVATIVES AS REDOX INDICATORS

The present invention is concerned with new redox indicators and with the preparation and use thereof.

The reaction of hydrogen peroxide with oxidation indicators, catalysed by peroxidase or peroxidate-effective substances, plays a special role in analytical chemistry because, apart from the detection of hydrogen peroxide and peroxidase, it also permits the determination of a series of substances which react with oxygen and a number of materials with the formation of hydrogen peroxide. In the following, some of the substances are set out and the corresponding oxidases are mentioned in brackets:

glucose (glucose oxidase), galactose (galactose oxidase), L-amino acids (L-amino acid oxidase), cholesterol (cholesterol oxidase), uric acid (uricase), sarcosine (sarcosine oxidase), glycerol (glycerol oxidase) and pyruvate (pyruvate oxidase).

As a detection reaction for peroxidases, the method is especially useful for the determination of haemoglobin.

These are, in particular, reactions which are of great importance in medical diagnosis and in foodstuff chemistry.

The detection reactions are carried out either in a cuvette or with the help of dry reagent carriers. Quantification thereby takes place with photometers via a transmission measurement, with remission photometers via a remission measurement or with the help of comparative colours by visual comparison.

The use of dry reagent carriers, i.e. absorbent or swellable carriers which are impregnated with the reagents or into which the reagents are incorporated via other steps and on which, after moistening with the substrate, the detection reaction takes place, has recently assumed over greater importance. These devices make possible, by means of a simple handling, a decisive rationalisation of the corresponding analyses with a simultaneous great saving of time.

The requirement to develop dry reagents in the case of which it is possible to use undiluted samples presents to the developer, with regard to the choice of the indicator or indicator system to be used, above all the problem that the serum or plasma (in the following referred to as serum) strongly disturbs the detection reaction. In particular, these disturbances make themselves noticeable when it is necessary to detect the substrates or enzyme activities via coupled reaction steps. An examples of substrates, there are here mentioned the detection of creatinine and uric acid and, as examples of activity determinations of enzymes, there are mentioned the determinations of creatine kinase, glutamate-oxalacetate transaminase (GOT) and glutamate-pyruvate transaminase (GPT).

Numerous compounds are known from the literature which can be used as indicators for the detection of hydrogen peroxide with peroxidase as catalyst. Such indicators include benzidine and benzidine derivatives, various phenols, polyphenols, for example guaic resin, leukodyestuffs, for example leakomalachite green, dichlorophenolindophenol, aminocarbazoles, triarylimidazoles and 2,2'-azino-di-(3-ethylbenzthiazole-6-sulphonic acid), as well as dyestuffs which result as coupling products of the oxidative coupling of aminoantipyrine or related compounds with phenols, naphthols, aniline derivatives and other coupling components.

In the case of the detection of hydrogen peroxide in undiluted serum samples, the above-mentioned known indicators display more or less strong disturbances by reaction with other serum components which simulate a higher or mostly lower concentration of the substrate to be detected. Some triarylimidazoles, such as those described in Federal Republic of Germany Patent Specification No. 27 35 690, are relatively little disturbed. However, the described imidazoles are only stable in the acidic pH range and, as experiments have shown, in the case of transmission into a weakly acidic to weakly alkaline pH range, as is necessary in the case of almost all enzymatic reactions, they are spontaneously oxidised by atmospheric oxygen, i.e. when they are present as the free base. Therefore, the production of functionable dry reagents using these indicators is only possible when they are embedded in a protective colloid, such as gelatine. However, this can only be done in special cases.

Therefore, it is an object of the present invention to provide dyestuff formers for the detection reaction for hydrogen peroxide or for peroxidate-active substances which do not react with the disturbing substances in the serum, are not spontaneously oxidised in the weakly acidic to alkaline range by atmospheric oxygen and thus can be used not only in cuvette tests but also in all matrices usable as dry reagent carriers.

Surprisingly, it has been found that compounds of the following general formula (I) satisfy the above-stated requirements.

Therefore, according to the present invention, there are provided imidazole derivatives of the general formula:

wherein R is a hydrogen atom, a tetrahydrofuranyl, cycloalkyl or alkyl radical, which can be substituted by hydroxyl, alkoxy, a sulphuric acid, phosphonic acid or carboxylic acid residue, as well as by a phenyl radical and $R_1$ and $R_2$, which can be the same or different, are julolidine radicals, tetrahydroquinoline radicals, which optionally carry on the nitrogen atom an alkyl radical which, in turn, can be substituted by a sulphuric acid, phosphonic acid or carboxylic acid residue, or radicals of the general formula:

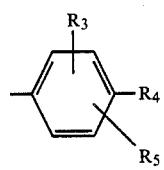

in which $R_4$ is a hydroxyl or amino group or a mono- or dialkylated amino group, in which the alkyl radicals can carry a sulphuric acid, phosphonic acid or carboxylic acid residue, and $R_3$ and $R_5$, which can be the same or different, are hydrogen atoms or alkyl or alkoxy radicals which are optionally substituted by a carboxyl group, with the proviso that $R_1$ and $R_2$ must not simultaneously be julolidine or tetrahydroquinoline and at least one $R_4$ of the substituents $R_1$ and $R_2$ must be a hydroxyl group; as well as the salts thereof.

The indicators of general formula (I) can be incorporated into all known detection systems.

The alkyl radicals in the substituents $R_1$, $R_2$, $R_3$, $R_4$ and $R_5$ contain 1 to 6 and preferably 4 carbon atoms, the methyl, ethyl, butyl and tert.-butyl radicals being preferred.

The alkoxy radicals in the substituents R, $R_3$ and $R_5$ contain 1 to 6 and preferably 1 to 4 carbon atoms, the methoxy and ethoxy radicals being preferred.

The cycloalkyl radical in the substituent R contains 3 to 8 carbon atoms, the cyclopropyl, cyclopentyl, cyclohexyl and cycloheptyl radicals being preferred.

The sulphuric acid, phosphonic acid and carboxylic acid residues, with which preponderantly the alkyl radicals are substituted, serve especially to improve the solubility.

With the indicators, there can be produced tests which are measured in a cuvette. For this purpose, the indicator, together with peroxidase, the enzyme(s) necessary for the particular parameter detection, other reagents, a buffer system, optionally a wetting agent and other adjuvants are lyophilised, mixed as a powder or pressed into tablets. The reagent mixture so obtained is, before use, dissolved in water to prepare the reagent solution. After the addition of a sample (substrate solution, enzyme solution, serum or plasma), the resultant colour is measured in a photometer and, from the molar extinction coefficient and the added reagent or sample volume, the particular concentration or enzyme activity is calculated. Not only kinetic but also end point measurements are possible.

Furthermore, the indicators, together with peroxidase, the reagents or other enzymes necessary for the particular parameter detection, the buffer system, optionally wetting agents and other adjuvants can be impregnated on to absorbent reagent carriers, for example papers, fleeces or the like. For this purpose, one or more impregnation solutions can be prepared in the form of aqueous or organic or mixed solutions, depending upon how the reagents or adjuvants dissolve. Carriers are impregnated or sprayed with these solutions and subsequently dried. The reagent carriers so obtained can be used as rapid diagnostic agents for the direct determination of component materials in, for example, body fluids. The body fluid is thereby applied directly to the reagent carrier or the carrier is dipped into the body fluid. By comparison of the resultant colour with comparison colours, a semi-quantitative determination is possible. By means of remission photometric processes, it is also possible to evaluate quantitatively. A reagent solution can also be prepared by elution of the reagents impregnated, as above described, on to a paper or fleece, using water or buffer, with which solution substrates or enzymes can be determined in a cuvette on a photometer, as described above (cf. Federal Republic of Germany Patent Specification No. 2,301,999).

A further possibility for the use of the indicators according to the present invention is their use in reagent films for the quantitative determination of enzymes or substrates by means of a remission photometer. The indicator, together with the other necessary reagents and adjuvants, is thereby worked up to give reagent films, for example according to the processes corresponding to those described in Federal Republic of Germany Patent Specifications Nos. 1,598,153 or 2,910,134.

Furthermore, it has been shown that the compounds according to the present invention can also be successfully combined with stabilisers, such as are described in Federal Republic of Germany Patent Specification No. 27 16 060. These stabilisers, which are 1-aryl semicarbazides, lead to the result that the finished tests become insensitive to the influence of light and that, with comparatively large amounts thereof, the function curves of the remission photometric measurements can be modulated.

As stated above, the indicators according to the present invention can be incorporated into all conventional reagent carriers, i.e. absorbent carriers, such as filter paper, fleeces or the like, or swellable or absorbent reagent films (see Federal Republic of Germany Patent Specification Nos. 15 98 153; 29 10 134 and 32 47 608). However, since they are preferably used for the detection of enzymes and substrates in serum, FIGS. 1 to 4 of the accompanying drawings illustrate in cross-section a series of devices which, according to Federal Republic of Germany Patent Specification No. 30 29 579, on the one hand separate from whole blood the serum or plasma necessary for the test and, on the other hand, because of the specially made construction of the reagent and adjuvant material layers, permit a temperature adjustment, pre-reaction and objective starting of the main reaction.

In detail these devices are constructed as follows:

FIG. 1:

On to an inert carrier foil 12 is fixed a layer 4 consisting of glass fibre which, on the one hand, serves for the transport of the serum and, on the other hand, for the separation of serum and erythrocytes. A further separation zone 5 consisting of glass fibre is fixed by means of a fixing mesh 6 partly covering over this layer 4. On to this mesh 6 is applied whole blood, which is separated in the zone 5 and the zone 4, respectively, into serum and erythrocytes, the latter being retained so that only serum passes over into the lefthand region of the zone 4. Laterally of the zone 4 there are fixed, via an adhesive connection 13, a thin synthetic resin fabric 3, as well as a carrier foil 1 consisting of a transparent synthetic resin. Under the carrier foil 1, there is, in turn, fixed a reagent zone 2 which consists either of a swellable or absorbent film into which are incorporated the reagents necessary for the reaction. A part of the reagents, especially those necessary for a prereaction, can already be contained in the zone 4. By pressure on the carrier foil 1, the reaction is started after the serum has completely filled the zone 4 which, by pressure contact, penetrates through the mesh 3 into the reagent zone 2 and uniformly moistens this through. If additional atmospheric oxygen is necessary for the reaction, after moistening through of the zone 2, the device can again be separated. The reaction is observed through the carrier foil 1 and evaluated on the basis of the coloration in the zone 2.

FIG. 2:

The construction of the zones serving for the obtaining of the serum corresponding to FIG. 1. In order to ensure a separation of the reagents, which possibly are not storage-stable with one another, two reagent papers 8 and 9 are provided which, together with the protective covering foil 7, are connected via adhesive point 13 to the carrier foil 12. Here again, after saturation of the zone 4 with serum, by pressure on the covering foil 7, a liquid contact of the reagent papers with the serum is brought about which brings about a mixing of the serum and of the reagents in the reagent papers 8 and 9, a reaction thereby taking place. It can be monitored through the covering foil 7.

FIG. 3:

This device again corresponds, in fundamental construction, to FIG. 1 but, instead of the intermediate fabric 3, there is provided an optical barrier layer 10. This barrier layer 10 is permeated with barium sulphate, titanium dioxide or similar strong-reflecting substances and usually consists of a synthetic resin or gelatine film. This layer 10 gives the result that, on the one hand, light beamed in for observation of the reaction is completey remitted and, on the other hand, any possible coloration of the zone 4 cannot become visible.

FIG. 4:

This again corresponds, with regard to the serum-obtaining part, to FIG. 1. The reagent zone 2, which here consists of a reagent film, is, in this case, applied to one side of a multifilar fabric 11 which, on the one hand, serves to stabilise the reagent film and, on the other hand, promotes the wetting by the serum and the admission of atmospheric oxygen. The fabric 11 and the loosely applied covering foil 7 are again fixed by an adhesive point 13 to the carrier foil 12. By means of pressure on the covering foil 7, there is produced a contact between the serum present in the zone 4 and the reagent zone 2, the reaction thereby being started.

Naturally, the possibility also exists of incorporating the compounds according to the present invention into gelatine matrices according to Federal Republic of Germany Patent Specification No. 2,735,690, together with the reagent and adjuvants necessary for the corresponding detection reaction.

Summarising, it is to be stated that the compounds of general formula (I) according to the present invention can be used in all test systems with the help of which hydrogen peroxide or peroxidate-active substances can be detected directly or after preceding reactions.

The compounds of general formula (I) according to the present invention can be prepared in known manner either by (a) condensing an α-diketone of the general formula:

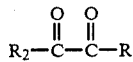
(II)

in which $R_2$ and R have the same meanings as in general formula (I), with an aldehyde of the general formula:

O=CH—$R_1$ (III)

in which $R_1$ has the same meaning as in general formula (I), with ammonia in acidic solution or (b) reacting an α-ketoxime of the general formula:

(IIa)

in which $R_2$ and R have the same meanings as in general formula (I), with an aldehyde of general formula (Ia) to give a compound of the general formula:

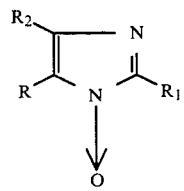
(Ia)

and reducing this compound or (c) reacting an acyl bromide of the general formula:

$R_2$—CO—CHR Br (IV)

in which $R_2$ and R have the same meanings as in general formula (I), with an amidine of the general formula:

(V)

in which $R_1$ has the same meaning as in general formula (I), in alkaline medium,
and subsequently, if necessary, the compound obtained is converted into a compound of general formula (I), or an imidazole base is converted into a salt or a salt is converted into a free base.

The conversion of the compounds obtained according to processes (a) to (c) into compounds of general formula (I) can take place, for example, by catalytic hydrogenation (nitro→amine), splitting off protective groups by hydrogenation with Pd/C (benzyloxy→hydroxy), hydrogenation of heterocycles (furanyl→tetrahydrofuranyl), fission of heterocycles by hydrogenation (tetrahydrofuranyl→4-hydroxybutyl) or reductive alkylation of amines (amines→dialkylamines).

By the reaction of 4-amino compounds of general formula (I) with a halomethane- or 2-ethane carboxylic acid, sulphonic acid or phosphonic acid or with a salt thereof in dimethylformamide, there are obtained the corresponding N-alkylaminomethane- or 2-ethane-acid radicals.

The reduction of N-oxides of general formula (Ia) can take place with zinc/acetic acid or with catalytically activated hydrogen.

The synthesis of the indicators according to general formula (I) takes place according to the method of B. Radzizewski in the form of its variant according to D. Davidson (see Org. Chem. 2, 319/1937). In some cases, instead of the α-diketone, according to Lettau Chem. 10, 431/1970; 11, 10/1971, it is more advantageous to use the corresponding α-ketoxime. The imidazole N-oxides resulting by the condensation with aldehyde and ammonium acetate in glacial acetic acid can be converted relatively easily and with good yields into the desired imidazoles. A further synthesis route is the reaction of amidines with substituted α-phenacyl bromides, as well as the ammonolysis of α-acyloxyketones (obtained by reaction of α-bromoketones with alkali metal salts of carboxylic acids in dimethylformamide) with ammonium acetate in glacial acetic acid. The action of gaseous hydrochloric acid on a mixture of α-aminonitrile and aldehyde or the corresponding benzylidene compound leads, with ring closure, to the corresponding imidazoles. Finally, the catalytic hydrogenation of heterocyclic radicals in diarylheterocyclic-substituted imidazoles is used for the preparation of corresponding perhydrogenated heterocycles and open-chained compounds. In the case of the reductive methylation of 4-aminoarylimidazoles with formaldehyde and catalytically activated hydrogen, the NH group on the imidazole ring is, surprisingly, not alkylated. On the contrary, there is obtained the corresponding N-dimethylamino compound. By conversion of the new imidazole bases into salts, for example hydrochlorides, methanesulphonates or the like, substantially stable indicators are obtained which are soluble in water and alcohols.

Preferred compounds according to the present invention include the following compounds:

(1) 2-(3,5-dimethoxy-4-hydroxyphenyl)-4-(5)-(4-dimethylaminophenyl)-5-(4)-n-butyl-(1H)-imidazole hydrochloride
(2) 2-(3,5-dimethoxy-4-hydroxyphenyl)-4-(5)-(4-dimethylaminophenyl)-5-(4)-tert.-butyl-(1H)-imidazole hydrochloride
(3) 2-(3,5-dimethoxy-4-hydroxyphenyl)-4-(5)-(4-dimethylaminophenyl)-5-(4)-(4-methoxybutyl)-(1H)-imidazole hydrochloride
(4) 2-(3,5-dimethoxy-4-hydroxyphenyl)-4-(5)-(4-dimethylaminophenyl)-5-(4)-cyclohexyl-(1H)-imidazole hydrochloride
(5) 2-(3,5-dimethoxy-4-hydroxyphenyl)-4-(5)-(4-dimethylaminophenyl)-5-(4)- benzyl-(1H)-imidazole hydrochloride
(6) 2-(3,5-dimethoxy-4-hydroxyphenyl)-4-(5)-(4-dimethylaminophenyl)-(1H)-imidazolyl-5-(4)-methanesulphonic acid
(7) 2-(3,5-dimethoxy-4-hydroxyphenyl)-4-(5)-(4-dimethylaminophenyl)-(1H)-imidazolyl-5-(4)-methanephosphonic acid
(8) 2-(3,5-dimethoxy-4-hydroxyphenyl)-4-(5)-(4dimethylaminophenyl)-(1H)-imidazolyl-5-(4)-acetic acid
(9) 4-(5)-(3,5dimethoxy-4-hydroxyphenyl)-5-(4)-methyl-(1H)-imidazolyl-2-(phenyl-4-N-methylamino-N-methane- and N-ethane-2-sulphonic acid)
(10) 4-(5)-(3,5-dimethoxy-4-hydroxyphenyl)-5-(4)-methyl-(1H)-imidazolyl-2-(phenyl-4-N-methylamino-N-methane and N-ethane-2-phosphonic acid)
(11) 4-(5)-(3,5-dimethoxy-4-hydroxyphenyl)-5-(4)-methyl-(1H)-imidazolyl-2-(phenyl-4-N-methylaminoacetic acid)
(12) 4-(5)-(3,5-dimethoxy-4-hydroxyphenyl)-5-(4)-methyl-(1H)-imidazolyl-2-(1,2,3,4-tetrahydroquinolino-6-methane and ethane-2-sulphonic acid)
(13) 4-(5)-(3,5-dimethoxy-4-hydroxyphenyl)-5-(4)-methyl-(1H)-imidazolyl-2-(1,2,3,4-tetrahydroquinolino-6-methane and ethane-2-phosphonic acid)
(14) 4-(5)-(3,5-dimethoxy-4-hydroxyphenyl)-5-(4)-methyl-(1H)-imidazolyl-2-(1,2,3,4-tetrahydroquinolino-6-acetic acid)
(15) 2-(3,5-dimethoxy-4-hydroxyphenyl)-5-(4)-methyl-(1H)-imidazolyl-4-(5)-(phenyl-4-N-methylamino-N-methane and ethane-2-sulphonic acid)
(16) 2-(3,5-dimethoxy-4-hydroxyphenyl)-5-(4)-methyl-(1H)-imidazolyl-4-(5)-(phenyl-4-N-methylamino-N-methane and N-ethane-2-phosphonic acid)
(17) 2-(3,5-dimethoxy-4-hydroxyphenyl)-5-(4)-methyl-(1H)-imidazolyl-4-(5)-(phenyl-4-N-methylaminoacetic acid)
(18) 2-[3,4-di-(tert.-butyl)-4-hydroxyphenyl]-5-(4)-methyl-(1H)-imidazolyl-4-(5)-(phenyl-4-N-methylamino-N-methane and ethane-2-sulphonic acid)
(19) 2-[3,5-di-(tert.-butyl)-4-hydroxyphenyl]-5-(4)-methyl-(1H)-imidazolyl-4-(5)-(phenyl-4-N-methylamino-N-methane and ethane-2-phosphonic acid)
(20) 2-[3,5-di-(tert.-butyl)-4-hydroxyphenyl]-5-(4)-methyl-(1H)-imidazolyl-4-(5)-(phenyl-4-N-methylaminoacetic acid)
(21) 4-(5)-(4-dimethylaminophenyl)-5-(4)-methyl-(1H)-imidazolyl-2-(5-[2-hydroxy-3-methoxyphenoxyacetic acid]).

The following Examples are given for the purpose of illustrating the present invention:

The extinction values and the extinction coefficients of the compounds described by way of example were determined according to the method described in Example 10.

In the above-mentioned Examples, as well as in the following Examples, the bracketed expressions (4) or (5) in the designation of the compounds signify the particular substituent position of the tautomeric form of the imidazoles of formula (I).

EXAMPLE 1

2-(3,5-Dimethoxy-4-hydroxyphenyl)-4-(5)-(4-dimethylaminophenyl)-5-(4)-methyl-(1H)-imidazole hydrochloride A mixture of 57.4 g. (0.3 mole) 1-(4-dimethylaminophenyl)-propane-1,2-dione, 60 g. (0.33 mole) 3,5-dimethoxy-4-hydroxybenzaldehyde (syringaldehyde) and 231 g. (3 mole) ammonium acetate are heated under reflux for 3 hours in 1 liter glacial acetic acid in an oil bath, while stirring and under an argon atomosphere. Thereafter, the reaction mixture is cooled to 15° C. and then dropped into 3.5 liters 7N ammonia (in the case of products which are difficult to filter off with suction, the reaction mixture is taken up in chloroform, shaken up with water, dried over anhydrous sodium sulphate and the solvent removed in a vacuum), whereafter the resultant crystal slurry is sharply filtered off with suction and the filter cake is washed with $3 \times 150$ ml. water. After drying the crude product over potassium hydroxide, the base is converted in methanol, with the addition of about 5N ethereal hydrochloric acid, into the hydrochloride. After recrystallisation from an appropriate solvent, for example glacial acetic acid/water (10/1 v/v), there are obtained 101.4 g. (71% of theory) of the title compound in the form of colourless crystals; m.p. 185°/219° C. (decomp.); $\lambda_{max}$ 680 nm ($\epsilon=25,500$).

In an analogous manner, by the reaction of the appropriate 1,2-diketones and aldehydes, there are obtained the following diarylimidazole derivatives:

(1a) 2-(4-hydroxyphenyl)-4-(5)-(4-dimethylaminophenyl)-5-(4)-methyl-(1H)-imidazole hydrochloride; m.p. 242° C. (decomp.); $\lambda_{max}$ 412 nm ($\epsilon=21,860$).

(1b) 2-[3,5-di-(tert.-butyl)-4-hydroxyphenyl]-4-(5)-(4-dimethylaminophenyl)-5-(4)-methyl-(1H)-imidazole hydrochloride; m.p. 255° C. (decomp.); $\lambda_{max}$ 650 nm ($\epsilon=41,830$).

(1c) 2-(4-hydroxyphenyl)-4-(5)-(3,5-dimethoxy-4-hydroxyphenyl)-5-(4)-methyl-(1H)-imidazole hydrochloride; m.p. 326° C. (decomp.); $\lambda_{max}$ 533 nm ($\epsilon=6,400$).

(1d) 2-[3,5-di-(tert.-butyl)-4-hydroxyphenyl]-4-(5)-(3,5-dimethoxy-4-hydroxyphenyl)-5-(4)-methyl-(1H)-imidazole hydrochloride; m.p. 296° C. (decomp.); $\lambda_{max}$ 673 nm ($\epsilon=29,800$).

(1e) 2-(3,5-dimethoxy-4-hydroxyphenyl)-4-(5)-(4-hydroxyphenyl)-5-(4)-methyl-(1H)-imidazole hydrochloride; m.p. 197°–199° C. (decomp.); $\lambda_{max}$ 533 nm ($\epsilon = 6,400$).

(1f) 2,4-(5)-di-(3,5-dimethoxy-4-hydroxyphenyl)-5-(4)-methyl-(1H)-imidazole hydrochloride; m.p. 158° C. (decomp.); $\lambda_{max}$ 590 nm ($\epsilon = 17,900$).

(1g) 2-(4-dimethylaminophenyl)-4-(5)-(4-hydroxyphenyl)-5-(4)-methyl-(1H)-imidazole hydrochloride; m.p. 225°–230° C. (decomp.); $\lambda_{max}$ 510 nm ($\epsilon = 10,500$)

(1h) 2-(4-dimethylaminophenyl)-4-(5)-(3,5-dimethoxy-4-hydroxyphenyl)-5-(4)-methyl-(1H)-imidazole hydrochloride; m.p. 182°–200° C. (decomp.); $\lambda_{max}$ 670 nm ($\epsilon = 10,800$).

(1i) 2-(6-N-methyl-1,2,3,4-tetrahydroquinolino)-4-(5)-(3,5-dimethoxy-4-hydroxyphenyl)-5-(4)-methyl-(1H)-imidazole hydrochloride; m.p. 190° C. (decomp.); $\lambda_{max}$ 700 nm ($\epsilon = 19,400$).

(1j) 2-(9-julolidino)-4-(5)-(3,5-dimethoxy-4-hydroxyphenyl)-5-(4)-methyl-(1H)-imidazole hydrochloride; m.p. 201° C. (decomp.); $\lambda_{max}$ 690 nm ($\epsilon = 25,399$).

(1k) 2-(4-hydroxy-3-methoxyphenyl)-4-(5)-(4-hydroxyphenyl)-5-(4)-methyl-(1H)-imidazole hydrochloride; m.p. >270° C. (decomp.); $\lambda_{max}$ 502 nm ($\epsilon = 3,730$).

(1l) 2-[3,5-di-(tert.-butyl)-4-hydroxyphenyl]-4-(5)-(4-hydroxyphenyl)-5-(4)-methyl-(1H)-imidazole; m.p. 200°–202° C. (decomp.); $\lambda_{max}$ 485 nm ($\epsilon = 6,700$).

(1m) 2-(3,5-dimethoxy-4-hydroxyphenyl)-5-(4)-methyl-(1H)-imidazolyl-4-(5)-(phenyl-4-amino-N-ethanesulphonic acid); m.p. >260° C. (decomp.); $\lambda_{max}$ 615 nm ($\epsilon = 27,500$).

(1n) 2-(3,5-dimethoxy-4-hydroxyphenyl)-5-(4)-methyl-(1H)-imidazolyl-4-(5)-(phenyl-4-amino-N-ethanephosphonic acid); m.p. >250° C. (decomp.); $\lambda_{max}$ 624 nm ($\epsilon = 25,600$).

(1o) 2-(3,5-dimethoxy-4-hydroxyphenyl)-5-(4)-methyl-(1H)-imidazolyl-4-(5)-(phenyl-4-aminoacetic acid); m.p. 124° C. (decomp.); $\lambda_{max}$ 620 nm ($\epsilon = 18,800$).

(1p) 2-[3,5-di-(tert.-butyl)-4-hydroxyphenyl]-4-(5)-(4-aminophenyl)-5-(4)-methyl-(1H)-imidazole; m.p. 228°–230° C.; $\lambda_{max}$ 576 nm ($\epsilon = 31,200$).

(1q) 2-[3,5-di-(tert.-butyl)-4-hydroxyphenyl]-5-(4)-methyl-(1H)-imidazolyl-4-(5)-(phenylaminoacetic acid); amorphous; $\lambda_{max}$ 614 nm ($\epsilon = 39,900$).

(1r) 2-[3,5-di-(tert.-butyl)-4-hydroxyphenyl]-5-(4)-methyl-(1H)-imidazolyl-4-(5)-phenylaminodiacetic acid; m.p. 225° C. (decomp.); $\lambda_{max}$ 580 nm ($\epsilon = 31,700$).

(1s) 2-(1-benzyl-1,2,3,4-tetrahydroquinolino)-4-(5)-(3,5-dimethoxy-4-hydroxyphenyl)-5-(4)-methyl-(1H)-imidazole; m.p. 190° C. (decomp.); $\lambda_{max}$ 705 nm ($\epsilon = 31,500$).

EXAMPLE 2

2-(3,5-Dimethoxy-4-hydroxyphenyl)-4-(5)-4-aminophenyl)-5-(4)-methyl-(1H)-imidazole hydrochloride 11 g. (0.05 mole) 1-(4-Acetylaminophenyl)-1-oximinopropan-2-one and 13.6 g (0.05 mole) 4-benzyloxy-3,5-dimethoxybenzaldehyde are dissolved, with the addition of 10 g. (0.13 mole) ammonium acetate, in 100 ml. glacial acetic acid and the reaction mixture is heated under reflux for two hours. Thereafter, 10 g. zinc dust are added portionwise, with stirring, and the reaction mixture boiled for a further two hours under argon. After standing overnight, the zinc acetate formed, which has crystallised out, is filtered off with suction and the filtrate is slowly mixed, while stirring and cooling, with 0.5 liter concentrated ammonia. The liberated imidazole base is taken up in dichloromethane, the solution is dried over anhydrous sodium sulphate and the solvent is evaporated off on a rotary evaporator to give 22.43 g. of crude base in the form of brownish crystals. This product is dissolved in 200 ml. 6N hydrochloric acid and heated under reflux for 45 minutes. Upon cooling, there crystallise 15.1 g. (74.9% of theory) of the title compound in the form of colourless crystals; m.p. 250° C. (decomp.); $\lambda_{max}$ 580 nm ($\epsilon = 18,900$).

(2a)

2-(3,5-dimethoxy-4-hydroxyphenyl)-4-(5)-(4-amino-3-methoxyphenyl)-5-(4)-methyl-(1H)-imidazole hydrochloride In the same way as described in the above Example 2, from 1-(4-acetylamino-3-methoxyphenyl)-1-oximinopropan-2-one and 3,5-dimethoxy-4-hydroxybenzaldehyde, there is obtained 2-(3,5-dimethoxy-4-hydroxyphenyl)-4-(5)-(4-amino-3-methoxyphenyl)-5-(4)-methyl-(1H)-imidazole hydrochloride in the form of colourless crystals; m.p. 218° C. (decomp.); $\lambda_{max}$ 402 nm ($\epsilon = 15,400$).

EXAMPLE 3

2-(4-Aminophenyl)-4-(5)-(3,5-dimethoxy-4-hydroxyphenyl)-(1H)-imidazole hydrochloride (a) In a two-phase condensation, 4.0 g. (0.02 mole) 4-nitrobenzamidine hydrochloride in 30 ml. water and 5.5 g. (0.02 mole) ω-bromoacetosyringone in 50 ml. chloroform are reacted at 25° C. with vigorous stirring, with 20 ml. (0.04 mole) of a 2 molar aqueous potassium hydroxide solution and subsequently heated to the boil for about four hours. After separating off the chloroform phase, the aqueous phase is neutralised and extracted several times with chloroform. The combined organic phases are evaporated and the residue is purified column chromatographically on silica gel with ethyl acetate as elution agent, 1.2 g. 2-(4-nitrophenyl)-4-(5)-(3,5-dimethoxy-4-hydroxyphenyl)-(1H)- imidazole being obtained in the form of a colourless, amorphous material characterised by $^1$H-NMR spectroscopy. EI mass spectrometry and elementary analysis (yield 18% of theory).

(b) 1.0 g. (0.003 mole) of the above nitro compound in 50 ml. ethanol is hydrogenated in the presence of 0.1 g. 10% palladium-on-charcoal at 25° C. under normal pressure. After filtering off the catalyst, the filtrate is mixed with ethereal hydrogen chloride and evaporated. The residue is triturated with diethyl ether to give 0.7 g. of the title compound (yield 61% of theory); m.p. 285°–290° C.; $\lambda_{max}$ 560 nm ($\epsilon = 24,500$).

EXAMPLE 4

2-(4-Dimethylaminophenyl)-4-(5)-(3,5-dimethoxy-4-hydroxyphenyl)-(1H)-imidazole hydrochloride (a) A suspension of 6.4 g. (0.018 mole) 4-benzyloxy-3,5-dimethoxy-ω-bromoacetophenone and 3.3 g. (0.018 mole) sodium 4-N,N-dimethylaminobenzoate in 150 ml. anhydrous dimethylformamide is heated to 130° C. for 1.5 hours, while stirring. Evaporation of the solvent and trituration of the residue with dichloromethane and finally with diethyl ether gives 4.2 g. 4-benzyloxy-3,5-dimethoxy-ω-(4-N,N-dimethylaminobenzoyloxy)-acetophenone in the form of a colourless powder (yield 53% of theory); m.p. 114° C.

(b) 30 g. (0.067 mole) of the ester obtained according to the above process are heated in 150 ml. glacial acetic acid with 51.4 g. (0.67 mole) ammonium acetate, while stirring, for two hours to 130° C. After cooling, the reaction mixture is poured on to one liter of ice water and extracted several times with ethyl acetate. The combined ethyl acetate extracts are washed with dilute aqueous sodium hydroxide solution, dried and evaporated. The residue is purified by column chromatography on silica gel, eluting first with toluene/ethyl acetate (9/1 v/v) in order to separate off less polar components, and then with toluene/ethyl acetate/methanol (2/2/1 v/v/v). Evaporation of the appropriate fraction gives 5 g. 2-(4-dimethylaminophenyl)-4-(5)-(4-benzyloxy-3,5-dimethoxyphenyl)-(1H)-imidazole in the form of a colourless substance (yield 18% of theory); m.p. 196° C.

(c) 4.3 g. (0.01 mole) of the imidazole derivative thus obtained are hydrogenated in 100 ml. ethanol in the presence of 0.3 g. 10% palladium-on-charcoal at 25° C., under normal pressure. After removal of the catalyst, the solution is mixed with 1 ml. concentrated hydrochloric acid and evaporated to give 3.2 g. of the title compound (yield 70% of theory); $\lambda_{max}$ 626 nm ($\epsilon$=4,770).

EXAMPLE 5

2,4-(5)-Bis-(4-dimethylaminophenyl)-(1H)-imidazole hydrochloride (a)

4-dimethylaminobenzaldehyde-bisulphite adduct 10 g. (0.067 mole) 4-Dimethylaminobenzaldehyde are dissolved in 50 ml. toluene and vigorously stirred for six hours with 100 ml. saturated bisulphite solution. The resulting crystalline material is filtered off with suction and washed with 50 ml. toluene. Yield: 12.8 g. (75% of theory).

(b)

(4-Dimethylaminophenyl)-methylimino-(4-dimethylaminophenyl)-acetonitrile 12.1 g. (0.048 mole) Bisulphite adduct, 45 ml. concentrated ammonia and 2.6 g. (0.053 mole) sodium cyanide are stirred for 2 hours at 37° C. and then shaken up with 3×75 ml. dichloromethane. The organic phase is separated off, subsequently shaken three times with, in each case, 20 ml. water and evaporated. There are obtained 7.5 g. of a reddish oil which, after recrystallisation from 30 ml. isopropanol, gives 3.8 g. (26% of theory) of the title compound in the form of colourless crystals; m.p. 144°-146° C. (decomp.).

(c)

2,4-(5)-Bis-(4-dimethylaminophenyl)-(1H)-imidazole hydrochloride 3.5 g. (0.011 mole) of the acetonitrile derivative are dissolved in 40 ml. anhydrous dioxan, heated to the boil and, while stirring, hydrogen chloride gas is passed in for two hours. The amorphous hydrochloride thereby formed is separated off and dissolved in 25 ml. water. By the addition of concentrated ammonia and shaking up with 3×50 ml. dichloromethane, there are obtained 3.2 g. of amorphous crude product which is purified chromatographically on a silica gel 60 column with ethyl acetate-chloroform (2/1 v/v). The appropriate fractions are subsequently recrystallised from 20 ml. isopropanol to give 2.24 g. (73.2% of theory) of the title compound; m.p. 233° to 235° C.; $\lambda_{max}$ 764 nm ($\epsilon$=9,800).

EXAMPLE 6

2-(3,5-Dimethoxy-4-hydroxyphenyl)-4-(5)-(4-dimethylaminophenyl)-5-(4)-(2-tetrahydrofuryl)-(1H)-imidazole hydrochloride (a)

2-(3,5-Dimethoxy-4-hydroxyphenyl)-4-(5)-dimethylaminophenyl-5-(4)-(2-furyl)-(1H)-imidazole hydrochloride 72.9 g. (0.3 mole) 1,2-Dioxo-2-(4-dimethylaminophenyl)-1-furyl-(2)-ethane are heated under argon with 60.12 g. (0.33 mole) 3,5-dimethoxy-4-hydroxybenzaldehyde (GC 98%) and 231 g. (3 mole) ammonium acetate in 1.2 liters glacial acetic acid for four hours, with stirring and under reflux. Thereafter, the reaction mixture is allowed to cool and poured on to 3.6 liters ice water. Subsequently, it is shaken out with 4×500 ml. ethyl acetate and the combined ethyl acetate phases are stirred for 30 minutes with 50 g. zinc dust. After suction filtration and evaporation of the imidazole solution in a vacuum, the residue is dissolved in 150 ml. methanol and the solution is dropped, under a protective gas, into 1 liter water. The crystals formed are filtered off with suction and dried to give 113.2 g. of pale green-grey coloured imidazole compound which is further purified on a silica gel column, using chloroform/methanol (12/1 v/v). The appropriate fractions contain 57.5 g. of crude imidazole. After stirring with 300 ml. acetone, there are obtained 50 g. (41.1% of theory) of colourless imidazole. After eluting the column with methanol and working up of the mother liquor, a further 15.6 g. of slightly contaminated product are obtained, the total yield being 54% of theory. By adding 50 ml. 5N ethereal hydrochloric acid to a suspension of the imidazole base in 100 ml. ethanol, solution first takes place, followed by crystallisation, which is completed by placing in an icebath. There are obtained 53.2 g. of the almost colourless hydrochloride of title compound; m.p. 172° C. (decomp); $\lambda_{max}$ 680 nm ($\epsilon$=12,342).

(b)

10.9 g. (0.021 mole) of the compound obtained above are dissolved in 250 ml. analytical grade methanol and, with the addition of 1.5 g. palladium sponge, hydrogenated for six hours at 36° to 38° C. under normal pressure. The reaction mixture is worked up in the usual way and the crude product is purified by column chromatography in silica gel 60 with chloroform/methanol (5/1 v/v) to give 1.24 g. (13.6% of theory) of a beige-coloured, chromatographically uniform crystallisate of the title compound; m.p. 98° C./110° C. (decomp.) (no clear melting point).

TLC finished plate; silica gel; elution agent: chloroform-methanol (5/1 v/v), $R_f$=0.36; $\lambda_{max}$ 680 nm ($\epsilon$=16,700).

EXAMPLE 7

2-(3,5-Dimethoxy-4-hydroxyphenyl)-4-(5)-(4-dimethylaminophenyl)-5-(4)-(4-hydroxybutyl)-(1H)-imidazole hydrochloride 16 g. (0.023 mole) of the title compound of Example 6 are hydrogenated in 400 ml. methanol with the addition of 2 g. palladium sponge for eight hours at 36° to 38° C. under normal pressure. The crude product obtained after working up is purified on silica gel 60 with chloroform-methanol (5/1 v/v) to give 4 g. of chromatographically uniform material which is dissolved in 50 ml. methanol, stirred for 30 minutes with 2 g. zinc dust and, by the addition of 20 ml. 5N ethereal hydrochloric acid, isolated as the hydrochloride. There are obtained 3.52 g. (21.8% yield) of the title compound in the form of colourless crystals; m.p. 140°/212° C. (decomp.); $\lambda_{max}$ 640 nm ($\epsilon=25,000$).

EXAMPLE 8

2-(3,5-Dimethoxy-4-hydroxyphenyl)-4-(5)-(4-dimethylaminophenyl)-5-(4)-methyl-(1H)-imidazole hydrochloride 5 g. (0.0126 mole) of the title compound of Example 2 are suspended in 140 ml. methanol and, after the addition of 0.7 ml. concentrated hydrochloric acid and 0.5 g. platinum oxide, as well as of 3.3 ml. 37% formalin solution, hydrogenated for five hours at 5° to 10° C. After ending the take up of hydrogen, the reaction mixture is filtered off from the catalyst with suction, the filtrate is evaporated in a vacuum and the hydrogenation product, 5.95 g. of colourless crystals, is recrystallised from 150 ml. methanol to give 4.2 g. (70.1% yield) of colourless crystals of the title compound; m.p. 185°/218°–219° C. (decomp.); $\lambda_{max}$ 680 nm ($\epsilon=25,500$).

(8a)

2-(3,5-Dimethoxy-4-hydroxyphenyl)-4-(5)-(4-dimethylamino-3-methoxyphenyl)-5-(4)-methyl-(1H)-imidazole hydrochloride In a manner analogous to that described in Example 8, from the product of Example 2a there is obtained the above-mentioned title compound in the form of colourless crystals; m.p. 211° C. (decomp.); $\lambda_{max}$ 417 nm ($\epsilon=28,300$).

EXAMPLE 9

2-(3,5-Dimethoxy-4-hydroxyphenyl)-5-(4)-methyl-(1H)-imidazolyl-4-(5)-(phenyl-4-amino-N-mono- and bis-ethane-2-sulphonic acid)

3.3 g. (0.01 mole) 2-(3,5-Dimethoxy-4-hydroxyphenyl)-4-(5)-(4-aminophenyl)-5-(4)-methyl-(1H)-imidazole (base of Example 2) are dissolved in 50 ml. dimethylformamide, 2.11 g. (0.01 mole) sodium 2-bromoethanesulphonate are added thereto and the reaction mixture is heated under reflux for 7 hours under argon. After evaporating off the solvent in a vacuum, the oily residue is purified chromatographically on a silica gel 60 column (filling height 110 cm., diameter 5 cm.) using as elution agent isopropanol/n-butyl ether/water (5:3:2 v/v/v). By evaporation of the appropriate fractions, crude products are obtained which, after boiling up with water, give 1.3 g. of the mono and 0.6 g. of the bis title compound.

TLC finished plate silica gel 60-F-254.
R$_f$ value of the mono compound: 0.44.
UV: $\lambda_{max}$ 620 ($\epsilon=29,100$).
R$_f$ value of the bis compound: 0.28.
UV: $\lambda_{max}$ 610 ($\epsilon=28,400$).

EXAMPLE 10

Survey of the optical properties of the substances of the general formula I

For the determination of the molar extinction coefficients, the following procedure is used: $2\times10^{-2}$ mole of indicator of general formula I are dissolved in 100 ml. 0.1M hydrochloric acid. If a substance does not dissolve quantitatively, it is dissolved in a mixture of hydrochloric acid and methanol (9:1 v/v). 0.1 ml. of this solution is diluted with 10 ml. 0.1M phosphate buffer (pH 6.0). Of the so obtained indicator solution 10 μl. are pipetted into a mixture consisting of 10 μl. diluted $H_2O_2$ (100 μl. 30% hydrogen peroxide are diluted with water to 100 ml.), 10 μl. peroxidase solution (600 U peroxidase are dissolved in 1 ml. water) and 10 ml. 0.1M phosphate buffer (pH 6.0). The indicator is oxidised, the solution becoming coloured. After 60 seconds, a spectrum of the coloured solution is recorded and from the extinction values there is calculated the molar extinction coefficient. If the coloured dyestuff precipitates out, then a mixture of buffer, acetone or methanol (9:1 v/v) is used.

The hydrogen peroxide concentrations or the concentrations of substrates from which, by a preceding enzymatic reaction, hydrogen peroxide is formed as a reaction product, can also be determined by the same process from samples.

Examples of the utility of the redox indicators according to the present invention:

EXAMPLE 11

Test system for the detection of uric acid in aqueous solutions

On to a polyester film precoated with gelatine there is poured, with a wet film thickness of 300μ, a gelatine matrix of the composition given hereinafter and subsequently dried. Into 47.5 ml. 0.5M trisphosphate buffer (pH 7.2) are incorporated 8.4 g. gelatine, 0.25 g. Tween 20, 0.5 KU uricase, 0.5 KU peroxidase and 100 mg. of the indicator substance of Example 7, i.e. 2-(3,5-dimethoxy-4-hydroxyphenyl)-4-(5)-(4-dimethylaminophenyl)-5-(4)-(4-hydroxybutyl)-(1H)-imidazole hydrochloride. The so produced reagent film is further worked up to give a test system according to FIG. 1.

35 μl. uric acid solution are applied to the application zone. By pressing the reagent zone and the fabric on to the transport zone, the reaction is started. After 2 minutes, it is measured in a remission photometer (the fabric has the function of equalising the unevennesses of the glass fibre fleece).

The calibration curves obtained with the described system are given in the following Table:

| uric acid concentration | % remission |
|---|---|
| 3 mg/dl | 55.1 |
| 5 mg/dl | 49.3 |
| 7 mg/dl | 43.8 |
| 9 mg/dl | 39.5 |
| 11 mg/dl | 34.2 |
| 14 mg/dl | 31.3 |

EXAMPLE 12

Test system for the detection of creatinine in serum

An absorbent carrier (stencil paper of the firm Schöller und Hösch, surface weight 12 g/m², absorbency 50 ml/m²) is impregnated with a solution of 200 KU peroxidase and 1.2 g. collagen hydrolysate dissolved in 100 ml. 0.1M phosphate buffer (pH 8.0) and dried. In a second impregnation procedure, the pre-impregnated paper is post-impregnated with a solution consisting of 2 mMole of indicator substance of Example 7 in 100 ml. methanol and dried, reagent paper (8) being obtained.

For the production of reagent paper (9), the above-mentioned absorbent paper is impregnated with a solution of 5 KU sarcosine oxidase, 30 KU creatinine amidohydrolase, 40 KU creatinine amidinohydrolase and 0.5 g. Triton X 100 in 100 ml. 0.1M phosphate buffer (pH 8.0) and dried.

Figure 2:
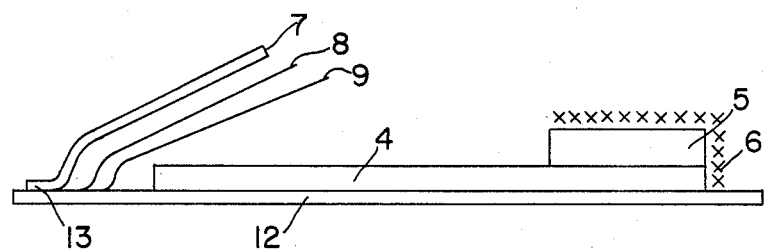

Both papers are then incorporated into a test system according to FIG. 2.

For the detection of creatinine in serum, 30 μl. of serum are pipetted on to the application zone. The reaction is started by pressing the enzyme and indicator paper on to the transport zone, colour obtained being measured by remission photometry after one minute. Evaluation takes place via a calibration curve.

In the following Table are given the values for a calibration curve for creatinine in serum:

| creatinine concentration | % remission |
|---|---|
| 0.1 mg/dl | 68.0 |
| 0.5 mg/dl | 57.2 |
| 1.5 mg/dl | 45.1 |
| 5.0 mg/dl | 32.7 |
| 10.0 mg/dl | 26.4 |

EXAMPLE 13

Test system for the detection of uric acid in blood

From the components set out below, there is produced a coating mass and, with a wet film thickness of 200μ, this is raked out on to a transparent foil and dried. 18 g. of a synthetic resin dispersion of a co-polymer of vinyl acetate and vinyl propionate, 1.38 g, alginate, 69 g. of a 0.45M tris-citrate buffer (pH 7.5), 0.47 g, indicator of Example 1, i.e. 2-(3,5-dimethoxy-4-hydroxyphenyl)-4-(5)-(4-dimethylaminophenyl)-5-(4)-methyl-(1H)-imidazole hydrochloride, 0.025 g. 1-(3-chlorophenyl)-semicarbazide, 0.025 g. $MgK_2EDTA.2H_2O$, 0.5 g. Triton X 100, 0.6 g. hexanol, 200 KU peroxidase and 2 KU uricase.

On to the so produced layer is raked on a second layer, with a layer thickness of 200μ, as optically white background of the composition given below and dried. This second layer is produced from 52 ml. 0.1M tris-citrate buffer (pH 7.0), 5.5 g. titanium dioxide, 2.7 g. diatomaceous earth, 0.4 g. alginate, 1.4 g. of a synthetic resin dispersion of a co-polymer addition of vinyl acetate and vinyl propionate and 0.2 g. Triton X 100.

Figure 3:
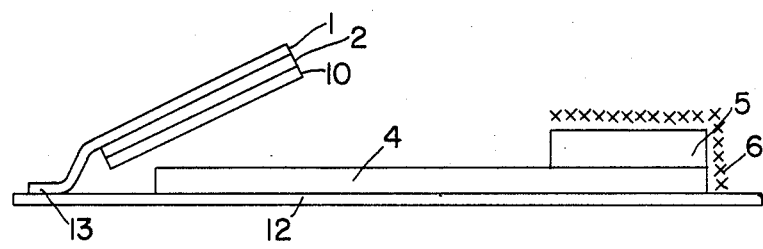

The so produced test film is worked up to give tests according to FIG. 3.

For the detection of uric acid in blood, 30 μl. blood are applied to the application zone, the reagent flap is, after one minute, pressed on and, after a further two minutes, the colour formed is measured with a remission photometer and the uric acid value determined from a previously produced calibration curve.

The values for the calibration curve are given in the following Table:

| uric acid concentration | % remission |
|---|---|
| 4.6 | 53.0 |
| 7.9 | 40.3 |
| 9.8 | 35.0 |
| 13.5 | 28.3 |

-continued

| uric acid concentration | % remission |
|---|---|
| 20.2 | 19.8 |

EXAMPLE 14

Test system for the detection of GOT in blood

In each case, one absorbent carrier (stencil paper of the firm Scholler und Hosch, surface weight 12 g/m$^2$, absorbency 50 ml/m$^2$) is impregnated with solutions 1 and 2 set out below and dried.

Solution 1: in 1 liter of a 0.2M buffer of aqueous potassium hydroxide solution and 2-(N-morpholino)ethanesulphonic acid (pH 6.7) are dissolved 0.03 mole α-ketoglutarate, 0.8 mole alaninesulphinic acid, 0.01 mole magnesium chloride, 0.0001 mole ascorbic acid, 0.009 mole compound of Example 1 and 5 g. octyl pyranoside to give reagent paper (8).

Solution 2: in 1 liter of the above-described buffer are dissolved 0.003 mole thiamine pyrophosphate, 500 KU pyruvate oxidase, 500 KU peroxidase and 100 KU ascorbate oxidase to give reagent paper (9).

These reagent papers are worked up to give a test system according to FIG. 2.

For the determination of the enzyme activity, 30 μl. blood are pipetted on to the application zone. After one minute, the covering foil and the reagent papers are pressed upon and the colour development monitored chronologically with a remission photometer. The evaluation takes place via a two point measurement from a reference curve. The reference curve is produced by preparing serial dilutions with enzyme activities of from 10 to 1000 U/liter and obtaining the remission values in a remission photometer via fixed time measurements.

EXAMPLE 15

Process for the detection of low glucose concentrations in the blood for the diagnosis of a hypoglycaemia A crude film mass is produced as follows: 10 g. of a 1.7% swollen alginate in a 0.5M phosphate buffer (pH 5.0), 15 g. aqueous synthetic resin dispersion of a co-polymer of vinyl acetate and vinyl propionate, 5 g. of a 15% aqueous solution of 4-dodecylbenzenesulphonate, 25 KU glucose oxidase, 200 KU peroxidase, 270 mg. compound of Example 1, 10 g. diatomaceous earth and 0.4 ml. hexanol are stirred to give a homogeneous slurry and raked, with a wet film thickness of 150μ, on to a multifilar fabric (2 F/964 of the firm Schweizer-Seidengaze Fabrik) and subsequently dried.

Figure 4:
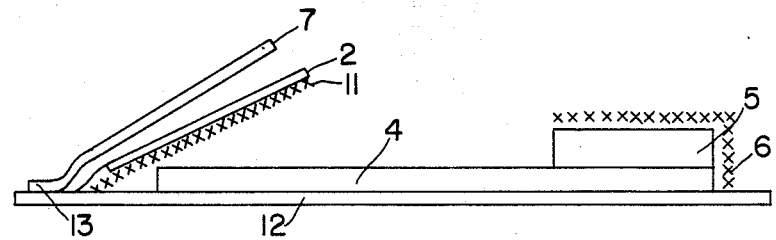

This film is worked up to give a test system according to FIG. 4. For the determination of the glucose, 30 μl. blood are pipetted on to the application zone, the covering foil and the reagent film are pressed on to the transport zone and the resulting reaction colour is measured with a remission photometer. The glucose concentrations are determined on the basis of a calibration curve, the values of which are given below:

| mg. glucose/dl. | % remission |
|---|---|
| 20 | 28.7 |
| 40 | 17.6 |
| 60 | 12.4 |
| 80 | 9.6 |

REFERENCES USED IN THE ACCOMPANYING DRAWINGS 1. reagent zone carrier (transparent)
2. reagent zone
3. fabric
4. transport zone of glass fibres
5. separation zone of glass fibres
6. fixing fabric
7. covering foil (transparent)
8. reagent paper (a)
9. reagent paper (b)
10. optically white background
11. multifilar fabric
12. carrier foil
13. adhesion point.

We claim:

1. An imidazole derivative of the formula

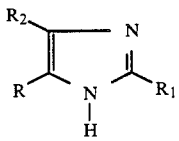

(I)

wherein R is a hydrogen atom, a tetrahydrofuranyl, cyclololweralkyl or loweralkyl radical, which can be substituted by hydroxyl, loweralkoxy, a sulphuric acid, phosphonic acid or carboxylic acid residue, as well as by a phenyl radical, and $R_1$ and $R_2$, which are different, are julolidine radicals attached at C9, tetrahydroquinoline radicals attached at C6, which optionally carry on the nitrogen atom a loweralkyl radical which, in turn, can be substituted by a sulphuric acid, phosphonic acid or carboxylic acid residue, or radicals of the formula:

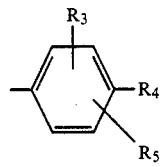

in which $R_4$ is a hydroxyl or amino group or a mono- or diloweralkoxylated amino group, in which the loweralkyl radicals can carry a sulphuric acid, phosphonic acid or carboxylic acid residue, and $R_3$ and $R_5$, which can be the same or different, are hydrogen atoms or loweralkyl or loweralkoxy radicals which are optionally substituted by a carboxyl group, with the proviso that $R_1$ and $R_2$ cannot simultaneously be julolidine or tetrahydroquinoline and at least one $R_4$ of the substituents $R_1$ and $R_2$ must be a hydroxyl group; or a salt thereof.

2. A compound of claim 1, where $R_1$ is julolidine or tetrahydroquinoline, wherein the nitrogen atom of said tetrahydroquinoline carries loweralkyl radical which may be substituted by a sulfuric, phosphonic or carboxylic acid residue.

3. A compound of claim 1, wherein $R_2$ is a julolidine or tetrahydroquinoline radical, optionally carrying on the nitrogen atom of said radical loweralkyl radical said loweralkyl radical optionally substituted by a sulfuric, phosphonic or carboxylic acid residue.

4. A compound of claim 1, wherein $R_1$ is the radical

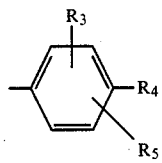

where $R_4$ is a hydroxyl, amino, or a mono or diloweralkylated amino group, and $R_3$ and $R_5$ may be hydrogen or loweralkyl or loweralkoxy groups, each of said groups optionally substituted by carboxyl.

5. A compound of claim 4, wherein $R_4$ is a mono or diloweralkylated amino group, further substituted by a sulfuric acid, phosphonic acid, or carboxylic acid residue on said loweralkyl groups.

6. A compound of claim 4, wherein $R_4$ is an hydroxy group.

7. A compound of claim 1, wherein R is hydrogen, tetrahydrofuranyl, cyclololweralkyl, or loweralkyl group.

8. A compound of claim 7, wherein R is loweralkyl group further substituted by a hydroxyl or loweralkoxy group, or a sulfuric acid, phosphonic acid, or carboxylic acid residue, or a phenyl group.

9. 2-(3,5-Dimethoxy-4-hydroxyphenyl)-4-(5)-(4-dimethyl-aminophenyl)-5-(4)-methyl-(1H)-imidazole.

10. 2-[3,5-Di-(tert-butyl)-4-hydroxyphenyl]-4-(5)-(4-dimethylaminophenyl)-5-(4)-methyl-(1H)-imidazole.

11. Reagent for the detection of hydrogen peroxide or a peroxidate-active substance, comprising a compound of claim 1 and a peroxidase.

12. Reagent according to claim 11, wherein said reagent is in the form of tablets, lyophilisates, impregnated reagent carriers or reagent films.

13. A method of detecting hydrogen peroxide or of a peroxide active substance which comprises adding to a sample containingg hydrogen peroxide or a peroxidate active substance a sufficient amount of a compound of claim 1 and a peroxidase to detect hydrogen peroxide or peroxidate active substances and detecting said hydrogen peroxide or peroxidate active substance thereby.

* * * * *